United States Patent
Donneys et al.

(10) Patent No.: US 11,762,184 B2
(45) Date of Patent: Sep. 19, 2023

(54) MICROSCOPE SURVEILLANCE SYSTEM

(71) Applicant: The Regents of the University of Michigan, Ann Arbor, MI (US)

(72) Inventors: Alexis Donneys, Ann Arbor, MI (US); Alexis Baker, Port Huron, MI (US); Steven R. Buchman, Novi, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 17/259,073

(22) PCT Filed: Jul. 9, 2019

(86) PCT No.: PCT/US2019/040943
§ 371 (c)(1),
(2) Date: Jan. 8, 2021

(87) PCT Pub. No.: WO2020/014188
PCT Pub. Date: Jan. 16, 2020

(65) Prior Publication Data
US 2021/0278652 A1    Sep. 9, 2021

Related U.S. Application Data

(60) Provisional application No. 62/695,471, filed on Jul. 9, 2018.

(51) Int. Cl.
*G02B 21/36* (2006.01)
*G02B 21/26* (2006.01)

(52) U.S. Cl.
CPC ........... *G02B 21/361* (2013.01); *G02B 21/26* (2013.01); *G02B 21/365* (2013.01)

(58) Field of Classification Search
CPC ..... G02B 21/361; G02B 21/26; G02B 21/365
USPC .......................................................... 348/79
See application file for complete search history.

(56) References Cited

U.S. PATENT DOCUMENTS

| | | | |
|---|---|---|---|
| 9,095,813 B2 | 8/2015 | Keith et al. | |
| 2013/0038727 A1 | 2/2013 | Clark | |
| 2014/0153916 A1* | 6/2014 | Kintner | H04N 13/243 396/419 |
| 2014/0158907 A1* | 6/2014 | Hamochi | H01J 37/20 250/442.11 |
| 2015/0070566 A1* | 3/2015 | Yoshida | G01C 11/02 348/349 |
| 2015/0233798 A1* | 8/2015 | Abeytunge | G02B 21/0088 435/29 |

(Continued)

FOREIGN PATENT DOCUMENTS

WO     WO 2016/161163     10/2016

OTHER PUBLICATIONS

International Search Report and Written Opinion for PCT/US19/40943. dated Sep. 30, 2019. 8 pages.

(Continued)

*Primary Examiner* — Allen C Wong
(74) *Attorney, Agent, or Firm* — CASIMIR JONES, S.C.; Tanya A. Arenson

(57) ABSTRACT

Provided herein are microscope surveillance systems and methods. In particular, provided herein are modular, multi-functional microscope surveillance systems and methods suitable for use in incubators and other environments.

19 Claims, 15 Drawing Sheets

(56) References Cited

U.S. PATENT DOCUMENTS

| | | | | |
|---|---|---|---|---|
| 2017/0368373 | A1* | 12/2017 | Sahadevan | A61M 1/3615 |
| 2018/0046065 | A1* | 2/2018 | Harvey | B63C 11/48 |
| 2018/0112164 | A1 | 4/2018 | Cecchi et al. | |
| 2018/0243913 | A1* | 8/2018 | Yamashita | B25J 19/023 |
| 2019/0256817 | A1* | 8/2019 | Gebhart | G01N 21/6428 |
| 2020/0318058 | A1* | 10/2020 | Mochizuki | C12M 41/48 |
| 2021/0214665 | A1* | 7/2021 | Blanchard | C12N 5/0634 |

OTHER PUBLICATIONS

Armstrong et al., Rapid CO2 capture from ambient air by sorbent-containing porous electrospun fibers made with the solvothermal polymer additive removal technique. AIChE Journal, 2019. 65(1), pp. 214-220.

Ghosh et al., Absorption of carbon dioxide into aqueous potassium carbonate promoted by boric acid. Energy Procedia. 2009. vol. 1(1): p. 1075-1081.

Keith et al., Climate Strategy with Co2 Capture from the Air. Climatic Change, 2006: 74(1-3), pp. 17-45.

Keith et al., A Process for Capturing CO2 from the Atmosphere. Joule, 2018. 2(8), pp. 1573-1594.

Smith et al., Pre-combustion capture of CO2—Results from solvent absorption pilot plant trials using 30wt% potassium carbonate and boric acid promoted potassium carbonate solvent. International Journal of Greenhouse Gas Control, 2012: 10, pp. 64-73.

* cited by examiner

Digital Microscope
Commercially available microscope can be focused using the MVS polar gantry.

Adjustable Magnification
Software controllable objective lens/optics wheels allows lenses to be swapped on a target by target basis, providing customizable magnification at different points throughout the petri dish.

MICROSCOPE SURVEILLANCE SYSTEM

This application is a national phase application under 35 U.S.C. § 371 of PCT International Application No. PCT/US2019/040943, filed Jul. 9, 2019, which claims priority to U.S. provisional patent application Ser. No. 62/695,471, filed Jul. 9, 2018, which is incorporated herein by reference in their entireties.

FIELD

Provided herein are microscope surveillance systems and methods. In particular, provided herein are modular, multi-functional microscope surveillance systems and methods suitable for use in incubators and other environments.

BACKGROUND

Live cell imaging is the study of living cells using time-lapse microscopy. It is used by scientists to obtain a better understanding of biological function through the study of cellular dynamics. Live cell imaging was pioneered in the first decade of the 20th century. One of the first time-lapse microcinematographic films of cells ever created was by Julius Ries, showing the fertilization and development of the sea urchin egg. Since then, several microscopy methods have been developed which allow researchers to study living cells in greater detail with less effort.

Examples of microscopy used for live cell imaging include phase contrast, fluorescence, and quantitative phase contrast microscopy. Existing systems do not sufficiently address the fact that many cell types must be cultured in incubators that have controlled temperature, humidity, and other environmental conditions. Imaging such cells often requires removal of the cells from the incubator to a separate imaging system, which risks contamination, and for any prolonged imaging, having the cells imaged in an environment that does not represent physiological conditions.

There have been attempts to combine imaging systems with incubators. However, these systems are often unduly expensive, difficult to run and maintain, and limited in capabilities. Additional systems and methods for imaging live cells are needed.

SUMMARY

Provided herein are microscope surveillance systems and methods. In particular, provided herein are modular, multi-functional microscope surveillance systems and methods suitable for use in incubators and other environments.

The systems and methods of the present disclosure provide a modular, interchangeable, incubator-safe surveillance system. The system finds use in a variety of cell culture and analysis applications.

For example, in some embodiments, provided herein is an imaging system comprising: a) a plurality of imaging modules (e.g., the same or different modules) configured for use with an incubation component (e.g., configured for individual insertion into or removal from a cell incubator) and configured for image or video capture of a cell culture sample placed in proximity to a module; b) a user interface, external to the cell incubator; configured to receive image or video data from each of the plurality of different imaging modules; and optionally c) a module holder configured to individually position each of the plurality of imaging modules.

In some embodiments, the imaging modules comprise one or more components selected from, for example, a digital microscope camera in operable communication with a camera motion control component, a cell culture sample alignment component, a configurable optical element component, a computer processor, a light source, a power source, a communications component (e.g., Bluetooth or WiFi), or one or more climate protection elements. In some embodiments, such components are located internal or external to the imaging modules. In some embodiments, the modules operate completely self-sufficiently (e.g., the module holder is not utilized or required).

In some embodiments, the camera motion control component comprises a robotic element that is configured to move the camera in X, Y, and Z dimensions. In some embodiments, the robotic element comprises a cylindrical gantry. In some embodiments, the cell culture sample alignment component comprises a sample container mounting ring configured to attach to a sample container and a mounting component configured to align and attach to the sample container mounting ring (e.g., using a plurality of mounting balls).

The present disclosure is not limited to particular sample containers and is suitable for use with any number of dishes, flasks, or vessels. In some embodiments, the system is exemplified with a petri dish.

In some embodiments, the configurable optical element component comprises a software configurable optical element wheel in optical communication with the digital microscope camera. In some embodiments, the configurable optical element comprises a plurality of different objective lenses, filters, or half wheel plates. In some embodiments, the alignment of the configurable optical element is configured for operation remotely. In some embodiments, the system comprises a plurality of different configurable optical elements.

The present disclosure is not limited to particular configurations of incubation components. In some embodiments, the incubation component is an incubator that the modules are placed within. In some embodiments, the incubation component comprises external sources of $CO_2$ and $H_2O$ in operable communication with said module holder or one or more of the modules. In some embodiments, the incubation component comprises sources of $CO_2$ and $H_2O$ located inside one or more of the modules. Exemplary components of the incubation component include, but are not limited to, one or more of $CO_2$ valves, $CO_2$ extractor, $CO_2$ purifier, CO2 micro-pump, CO2 micro-plumbing, $H_2O$ valves. $H_2O$ dehumidifier, $H_2O$ purifier, $H_2O$ micro-pump, $H_2O$ micro-plumbing, $H_2O$ reservoir, electronics component, solenoid valves, heating coil, release valve, or one or more sensors (e.g., including but not limited to, temperature, humidity, or $CO_2$ sensors). In some embodiments, the incubation component further comprises a $CO_2$ capture component (e.g., a chemical $CO_2$ generation component and/or an ion exchange resin component). In some embodiments, the chemical $CO_2$ generation component comprises potassium hydroxide desiccants and a heating element. In some embodiments, the ion exchange resin component comprises a support coated with an ion exchange resin (e.g., basic resin) and a water source and optionally one or more of a rotation component, a roller, or a heat source.

In some embodiments, the climate protection elements comprise waterproof casing for the module. In some embodiments, the digital microscope camera is waterproof.

In some embodiments, the computer processor is configured for wired or wireless communication with the user interface. In some embodiments, the system comprises at least 2 (e.g., 2, 3, 4, 5, 6, 7, 8, 9, 10 or more), distinct or the same or a combination thereof, imaging modules. In some embodiments, the different imaging modules are configured to perform one or more of visible light microscopy and fluorescence microscopy. In some embodiments, the modules are independently configured to collect qualitative or quantitative data and transmit the data to the user interface. In some embodiments, the module holder is a platform. In some embodiments, the platform is configured to rotate. In some embodiments, the platform is waterproof. In some embodiments, the module holder is integrated into the incubator. In some embodiments, the user interface is, for example, a laptop computer, a desktop computer, a tablet, a smart watch, or a smart phone. In some embodiments, the system is configured to obtain images or video of the sample at a predetermined interval. In some embodiments, the system is configured to obtain images or video of a selected portion of the sample. In some embodiments, the system is configured to independently image all or a portion of each of the modules.

In some embodiments, one or more of the modules comprises a dome light at the top of the module. In some embodiments, the dome light comprises a ring of light emitting diodes (LEDs,) and a highly-reflective spherical dome. In some embodiments, the LEDs comprise LEDs of different wavelengths. In some embodiments, the dome provides both uniform lighting, as well as highly oblique lighting, allowing the user to effectively illuminate the samples from the side, providing a method for achieve "digital phase contrast" imaging, without the need for additional complicated and expensive optical elements.

In some embodiments, the user interface comprises software configured to perform one or more functions selected from, for example controlling the frequency and location of images of the cell culture, analyzing image data, and controlling the operation of the modules and the module holder.

Further embodiments provide a method of imaging a cell culture sample, comprising: a) contacting the sample with a system as described herein; and b) collecting imaging data related to the sample using the system. In some embodiments, the method further comprises the step of analyzing the imaging data. In some embodiments, the analysis is one or more of annotating images or videos, calculating cell growth rates, assessing the presence of markers, or assessing gene expression.

Additional embodiments are described herein.

Definitions

Figure 1A:
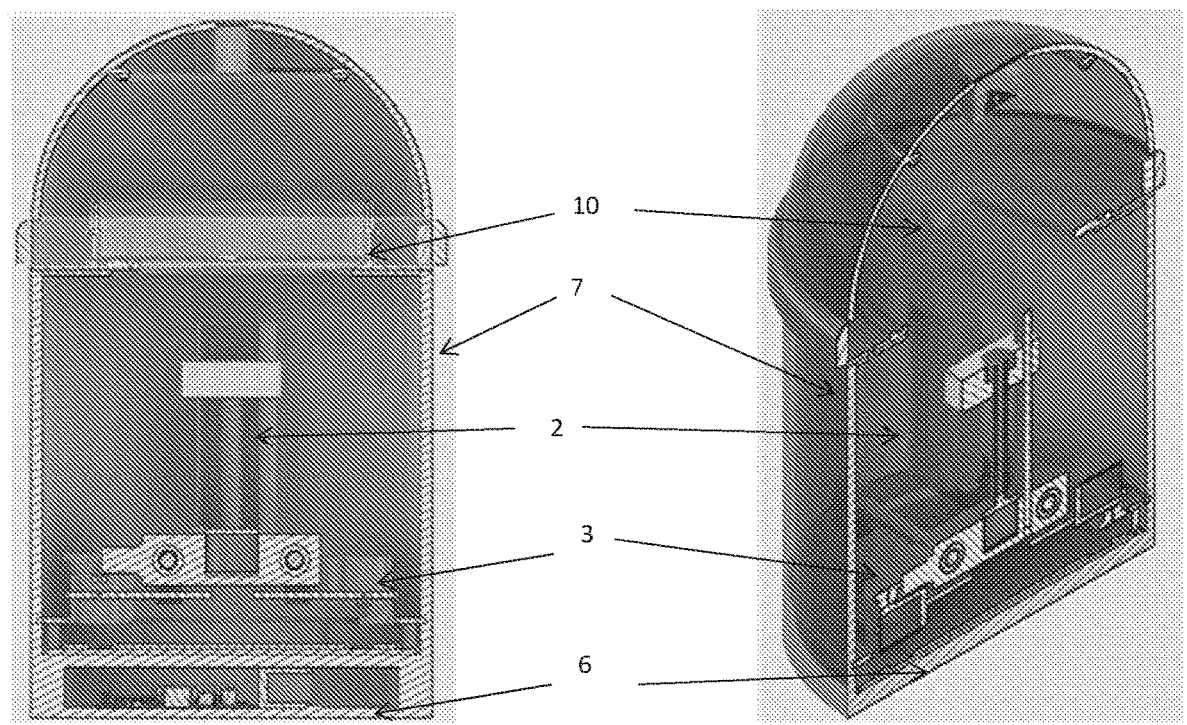
FIG. 1A shows an exemplary imaging module of embodiments of the present disclosure and FIG. 1B an exemplary camera motion control component of embodiments of the present disclosure.

To facilitate an understanding of the present disclosure, a number of terms and phrases are defined below, or terms may be defined elsewhere in the disclosure:

As used herein, the term "cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. Cells include cultured cells, including primary cultures, immortalized cells, stem cells, cell mixtures, genetically engineered or otherwise modified cells, and the like.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reactions that occur within a natural environment.

The term "sample" is used in its broadest sense. On the one hand, it is meant to include a specimen or culture. On the other hand, it is meant to include both biological and environmental samples. Biological samples may be animal, including human, fluid, cells, solid (e.g., stool) or tissue, as well as liquid and solid food and feed products and ingredients such as dairy items, vegetables, meat and meat by-products, and waste. Biological samples may be obtained from the various families of domestic animals, as well as feral or wild animals, including, but not limited to, such animals as ungulates, bear, fish, lagomorphs, rodents, etc. or combinations thereof.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound may be determined to be therapeutic by screening using the screening methods, devices, and/or systems of the present disclosure.

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape. In certain embodiments, the computer memory and computer processor are part of a non-transitory computer. In certain embodiments, non-transitory computer readable media is employed, where non-transitory computer-readable media comprises all computer-readable media with the sole exception being a transitory, propagating signal.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information e.g., data) from one location to another (e.g., from one device to another) using any suitable means.

DETAILED DESCRIPTION

Provided herein are microscope surveillance systems and methods. In particular, provided herein are modular, multi-functional microscope surveillance systems and methods suitable for use in incubators and other environments.

While surveillance systems and cameras both function to provide some form of live image capture, the technology which maintains the capacity to perform this function is principally different. Accordingly, a surveillance system serves a unique purpose and is intended for different means than a camera. Cameras are more individualized and perform an array of functions typically based on the impulses of the user. Surveillance systems are suited for constant and complete capture of multiple similar occurrences from multiple vantage points over long periods of time. Moreover, surveillance systems are suited for comparative imaging, where software can analyze occurrences within each image or video feed, analyze differences, and provide comparative datasets. In scientific research, it proves significant to capture data beyond what is under the discretion of a researcher at a moment in time. Still images may provide only one part or several disjointed parts of a story; surveillance, on the other hand, offers an uninterrupted, continuous stream of visual data so that key developments are captured.

During the course of development of embodiments of the present disclosure, obstacles in the development of a comprehensive microscopic surveillance system were overcome. There are inherent challenges to streamlining the concept of surveillance by joining multiple cameras into a single system. For example, the addition of microscopy to incubated settings adds an additional layer of complexity. Existing devices fail to address the intricacies that accompany the act of surveilling in microscopy. Below are some examples of obstacles encountered in the development and implementation of the present disclosure and the respective solutions implemented.

While embodiments of the invention can be implemented using a single imaging module, many uses of the system benefit from a plurality (e.g., 3, 4, 5, 6, etc.) of modules. Challenges included, but are not limited to, providing flexibility to use one or more imaging components (each, potentially configured to capture data in a different manner than the others), fitting multiple modules within the diversity of different space constraints provided by common incubators, providing quality imaging capabilities while protecting imaging modules from the environmental conditions (e.g., heat, humidity), processing multiple signals from multiple modules in a manner that permits a user to interact with the system from outside of the incubator, and establishing and managing diverse imaging experiments on live, cultured cells in an isolated, enclosed environment.

Multiplexing multiple systems within an incubator (hot/humid/water-jacketed metal box), and getting signal out was facilitated by development of a universal platform/data relay station/amplification antennae communication with an internet-based interface that is suitable for an incubated setting.

Space issues were addressed, in some embodiments, using theta- and R-motion drive trains to minimize spaces beyond vessel size.

In embodiments, sterility was obtained by, for example, embedded UV lighting. In some embodiments, high intensity UV lights within a module is turned on between experiments in order to sterilize internal components. In addition, in some embodiments, the entire device may be placed inside a UV "sleeve", which sterilizes the exterior of the module using an array of UV lights.

Extreme environments such as incubators or under water placement were addressed by climate/waterproofing modules, while developing design features that maintained modularity, imaging quality, and communication capability.

Modularity of the modules is achieved, for example, by individualizing each modules' motion and imaging using capacity-individual camera, drive train, and lighting. In some embodiments, modules are configured to provide user access and the ability to change light sources, filters, and cameras within modules. This allows for a multitude of interchangeable functionality in one system.

In some embodiments, inadvertent light diffusion and photo-bleaching caused by proximity of cameras is addressed by dome lighting.

In some embodiments, shock absorption components aid in avoiding unwanted motion artifacts and facilitate maintaining level cell cultures.

Repeatable relocation is obtained by honing devices, automated scope motion, and cell culture alignment components.

Smooth manual motion systems serve to move scopes micrometric distances based on, for example, a user trackpad or keyboard input and selection of suitable motors/gear ratios, servo controls, etc.

Exemplary components that serve to provide the above features and that address the multi-dimensional challenges are described herein.

I. Microscopic Video Surveillance System

Provided herein are modular, multi-functional microscope surveillance systems. In some embodiments, the microscope systems comprise a plurality of modules in operable communication with a module transport component and user interface. Each of these components is discussed in detail below.

A. Modules

In some embodiments, the system comprises one or more (e.g., 2, 3, 4, 5, 6, 7, 8, etc.) imaging modules. In some embodiments, an individual imaging module is self-contained and portable such that it is individually addable and removable from the system (e.g., from a system contained in an incubator). Each module comprises one or more of a digital microscope camera in operable communication with a camera motion control component, a cell culture sample alignment component, a configurable optical element component, a computer processor, a light source, and one or more climate protection elements.

An exemplary module 1 is shown in FIG. 1A. FIG. 1A shows camera 2 in operable communication with camera motion control element 3 (exemplified by a cylindrical gantry for motion control), sample alignment component 10 (exemplified with a 100 mm petri dish resting upon it), and climate protection elements 6 (exemplified by a waterproof connection to a platform (platform not shown)) and 7 (exemplified by a waterproof casing). Not shown in FIG. 1 is computer processor 4 and optional light source 5. Each of these elements is discussed in more detail below.

In some embodiments, the modules comprise a lighting source. The present disclosure is not limited to particular lighting sources. Examples include, but are not limited to, light emitting diodes (LEDs), fluorescent lights, halogen lights, incandescent lights, and the like.

Figure 2:
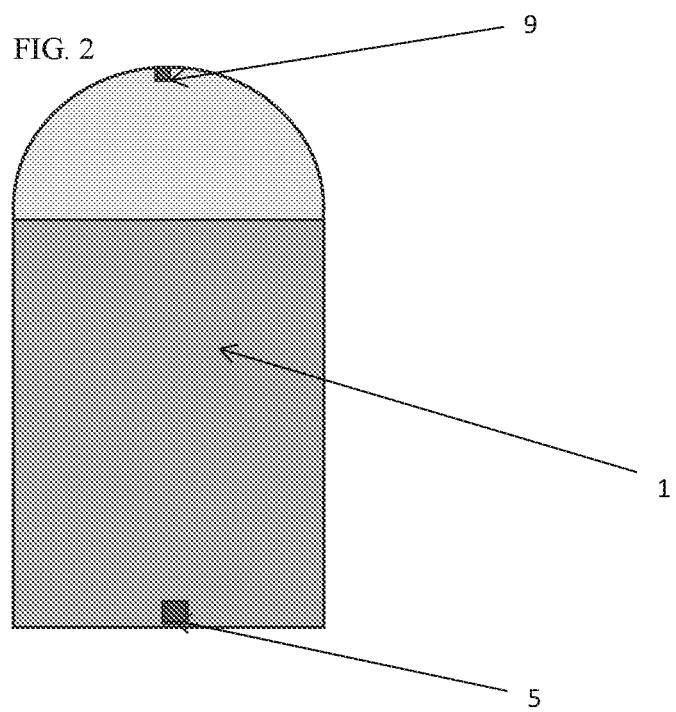
FIG. 2 shows a schematic of an exemplary lighting component of a module of embodiments of the present disclosure.

In some embodiments, the lighting source is located underneath the camera and sample compartment as shown by element 5 in FIG. 2.

In some embodiments, the lighting source is a dome light 9 as shown in FIG. 2. Uniform illumination of the sample container is important for obtaining high quality images. In some embodiments, the dome comprises a ring of high power LEDs, together with a highly-reflective spherical dome. This provides a uniform source of bright light illumination at the target wavelength. Domes with different wavelengths are possible, allowing the user to include ultraviolet (and other) illumination sources in order to perform fluorescence microscopy. In some embodiments, modules comprise both a dome light 9 and a light 5 placed underneath the camera and shown in FIG. 2.

Additionally, in some embodiments, a small, wide-angle camera 38 mounted at the apex of the dome can provide a continuous video stream of the entire petri dish, allowing users to identify interesting regions of the dish, and easily navigate to those places.

In some embodiments, the camera is a miniature, weatherproof/waterproof, high-resolution digital microscope camera. In some embodiments, the camera is coupled to a CCD or CMOS chip. The present disclosure is not limited to particular cameras. In some embodiments, the camera is a commercially available digital microscope camera (e.g., available from Olympus or other commercial suppliers or retailers). In some embodiments, cameras with high resolutions, such as the 18 MegaPixel AMScope, or the Lorex 4k Ultra HD may be used. In addition, certain applications (e.g., fluorescence video microscopy) utilize cameras with sensitivity to different wavelengths, such as the Tenum 640 uncooled thermal infrared camera. In some embodiments, Thorlabs scientific-grade cameras are used. They are designed specifically for microscopy applications, and provide low noise, high quantum efficiency, fast framerates, and sensitivity across a range of relevant wavelengths.

Figure 1B:
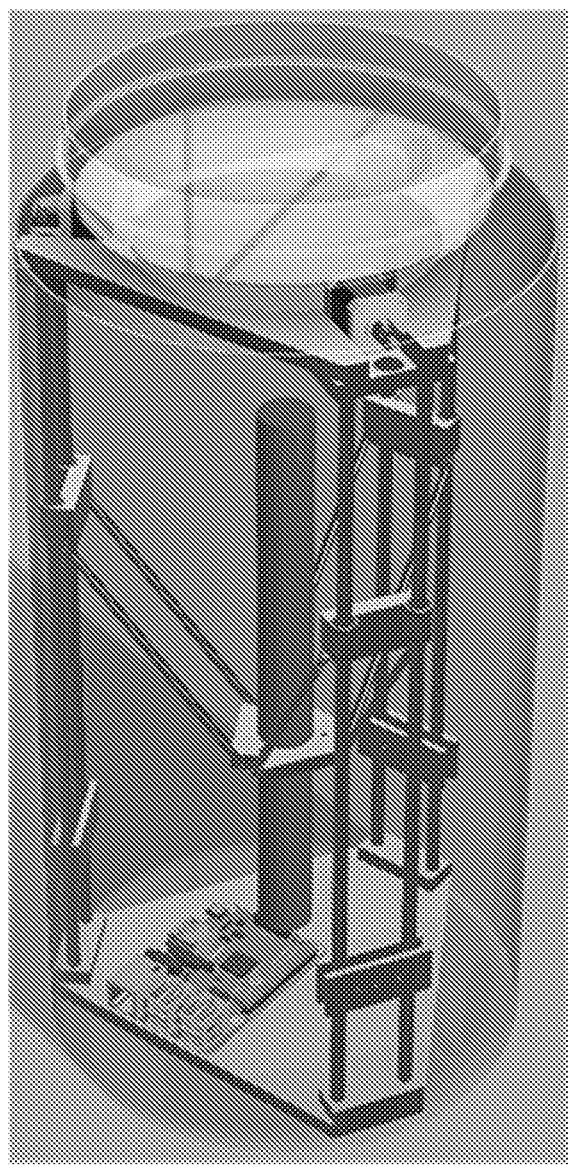

In some embodiments, the camera is in operable communication with a camera motion control component 3. The present disclosure is not limited to particular camera motion control components. The camera motion control component serves to move the camera in a plurality of dimensions (e.g., one or more or all of x, y, and z dimensions) in order to optimize image capture and to allow precise control of the camera location to execute an imaging program requested by a user (e.g., monitoring one or more sub-locations of a culture dish at one or more different time points). In some embodiments, the camera motion control component is a delta robot as shown in FIG. 1B. The delta robot utilizes a plurality of robotic arms and gears to move the camera in all three dimensions. In some embodiments, delta robots are generated by 3D printing, other fabrication techniques, or are commercially available (e.g., the Pocket Delta Robot by Asyril: www.asyril.com/en/products/delta-robots.html or the Mini Delta Robot by Omron Industrial Automation: industrial.omron.us/en/products/x-delta).

In some embodiments, the camera motion component comprises a cylindrical gantry 20 as shown in FIG. 3. The gantry allows the camera to translate n polar-coordinate fashion) in the horizontal plane, and translate linearly along the z-axis. This geometry provides full 3-dimensional motion in a maximally-compact space and is much more compact than a traditional XYZ translation stage. In some embodiments, the user interface utilizes an algorithm that allows a user to transparently control microscope motion in rectangular coordinates, despite the underlying cylindrical gantry and its intrinsically polar coordinate system. The dimensions of an exemplary cylindrical gantry are shown in FIG. 3A (left panel). An overview of a cylindrical gantry 20 within a module is shown in the right panel of FIG. 3A.

In Operation, the cylindrical gantry moves in the theta, R, and Z direction (polar coordinates). To move in the theta direction (FIG. 3B), a first stepper motor 21 engages with an outer gear 22 and a flush roller platform 23 rolls across three roller bearings 24. The gears maintain traction from a central pivot pipe 25. Electronics are fed through the central pivot pipe.

Figure 3A:
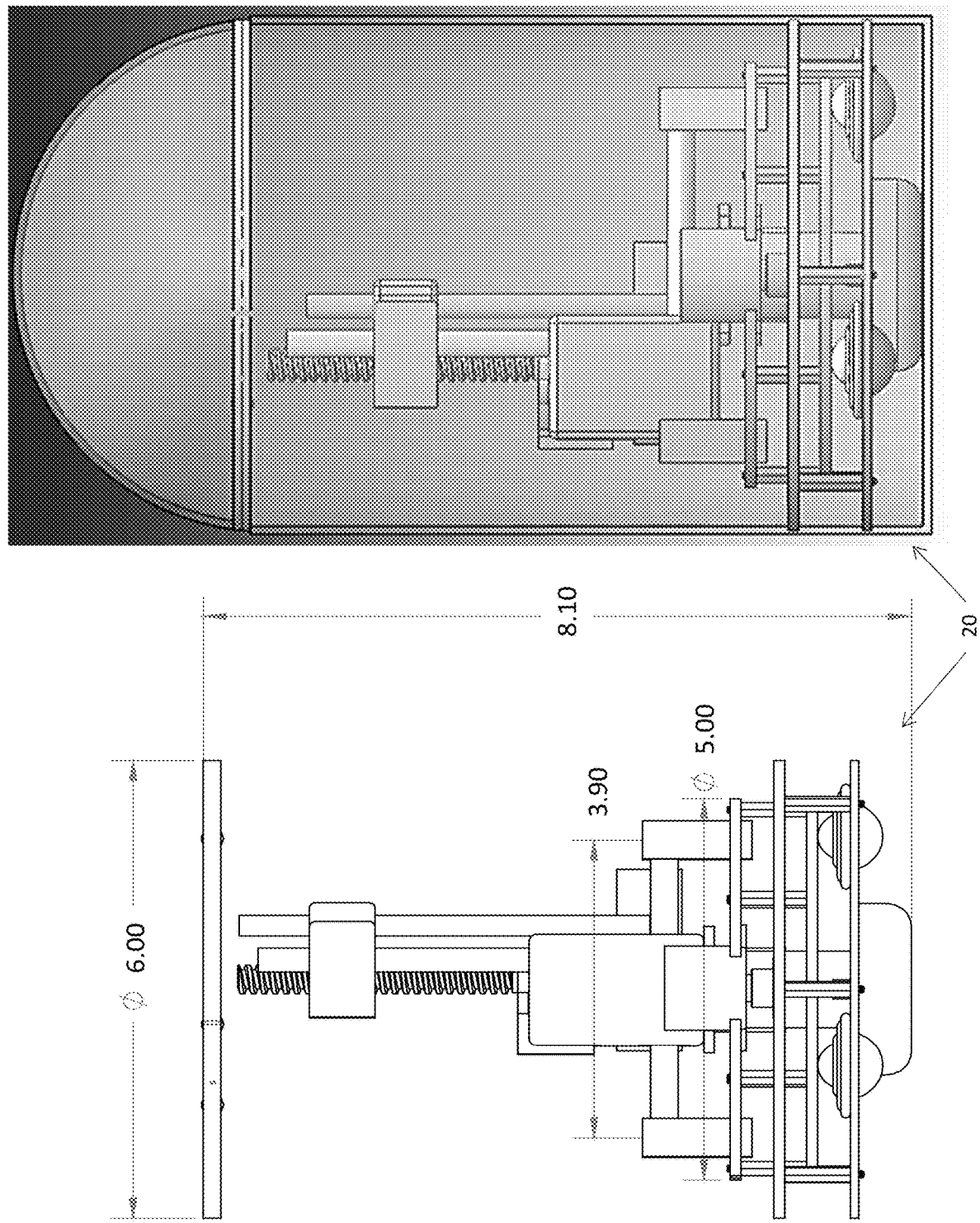
FIG. 3A-FIG. 3D shows exemplary cylindrical gantry camera motion control components of embodiments of the present disclosure.
Figure 3B:
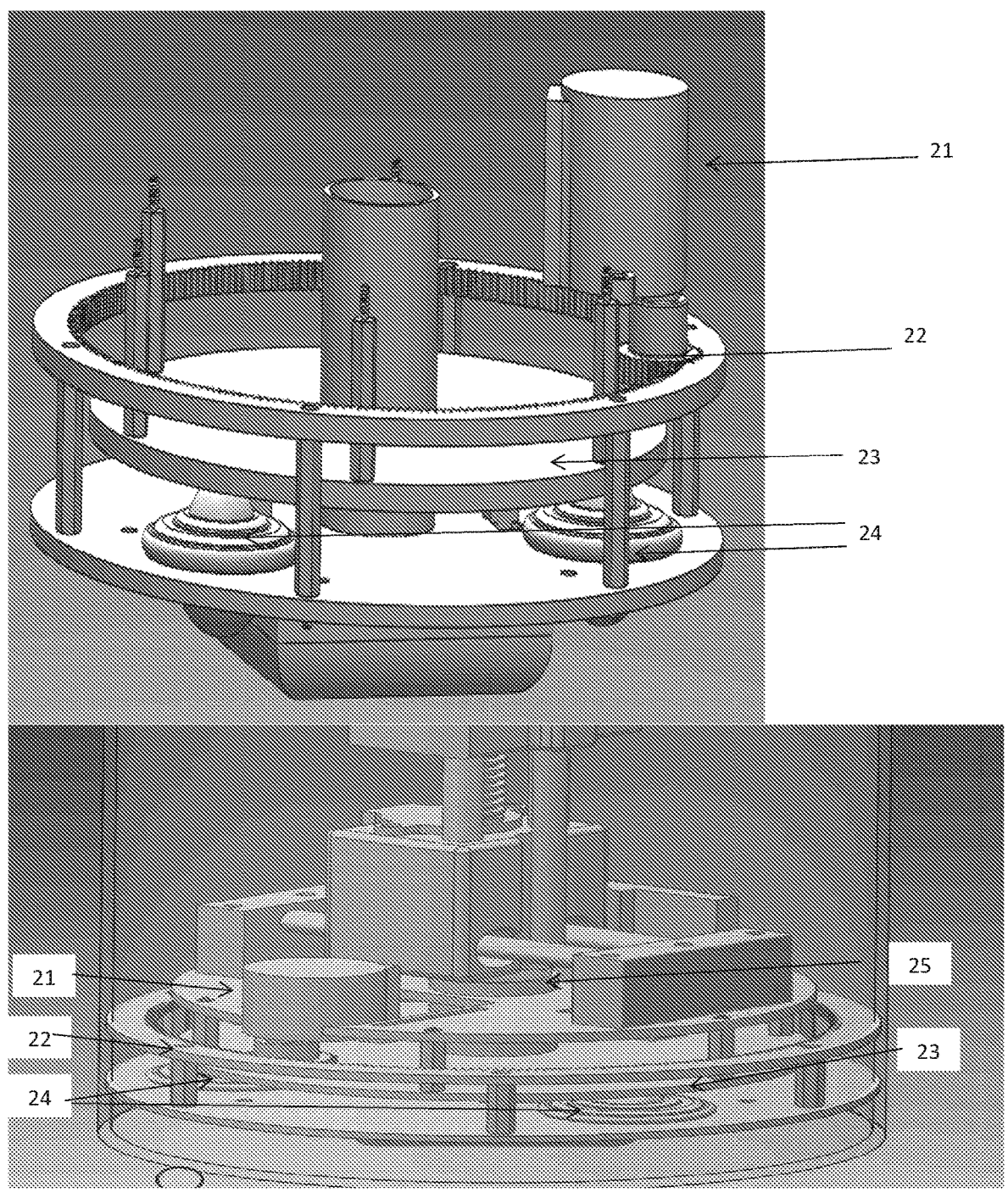
Figure 3C:
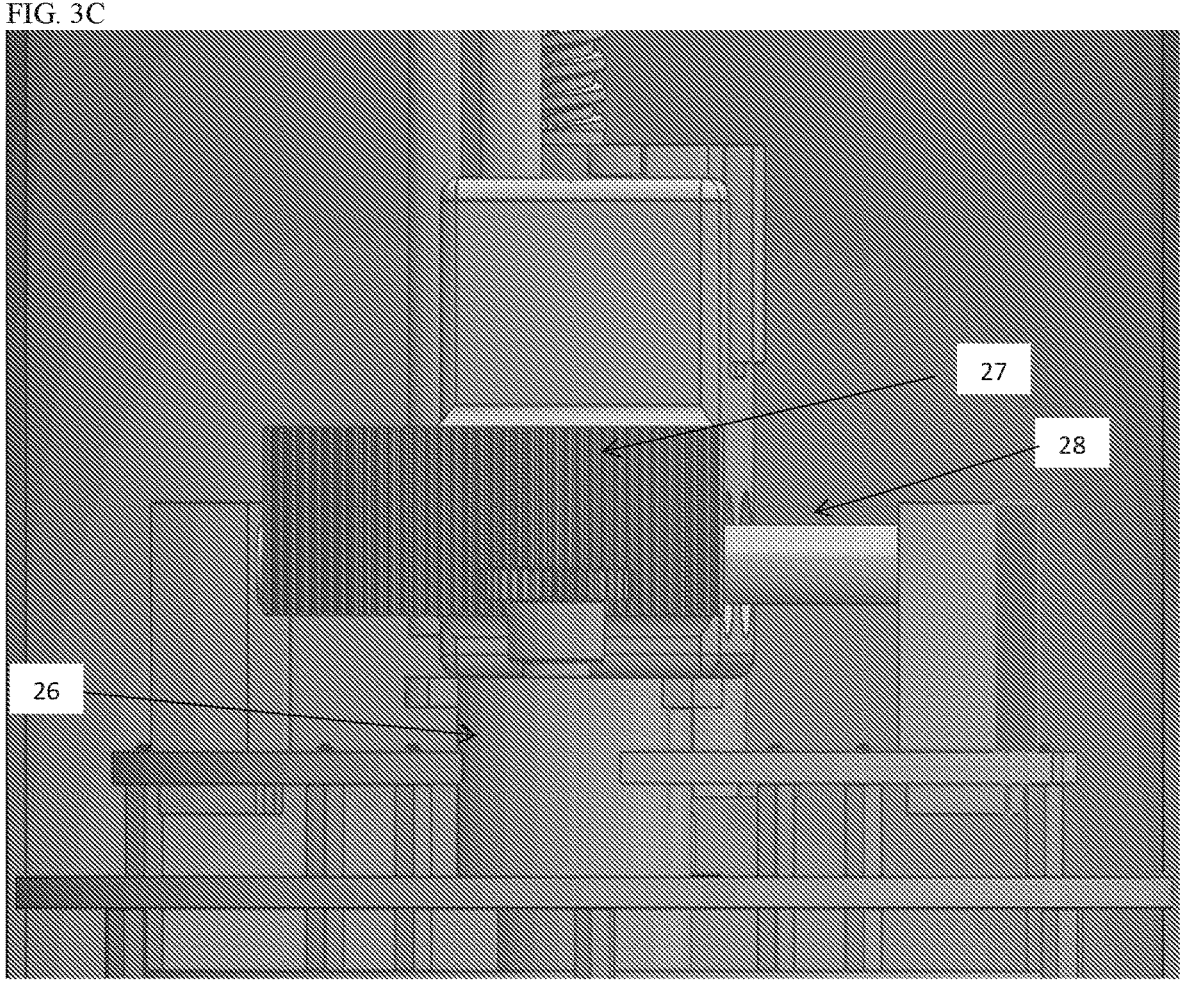

R motion is shown in FIG. 3C. A second stepper motor 26 engages with gear mesh 27 on linear carriage 28 and the gear drives the carriage forward and backward 50% of the distance. To achieve 100% coverage of the sample, theta rotates to give R access to the other half of the culture container (e.g., petri dish).

Figure 3D:
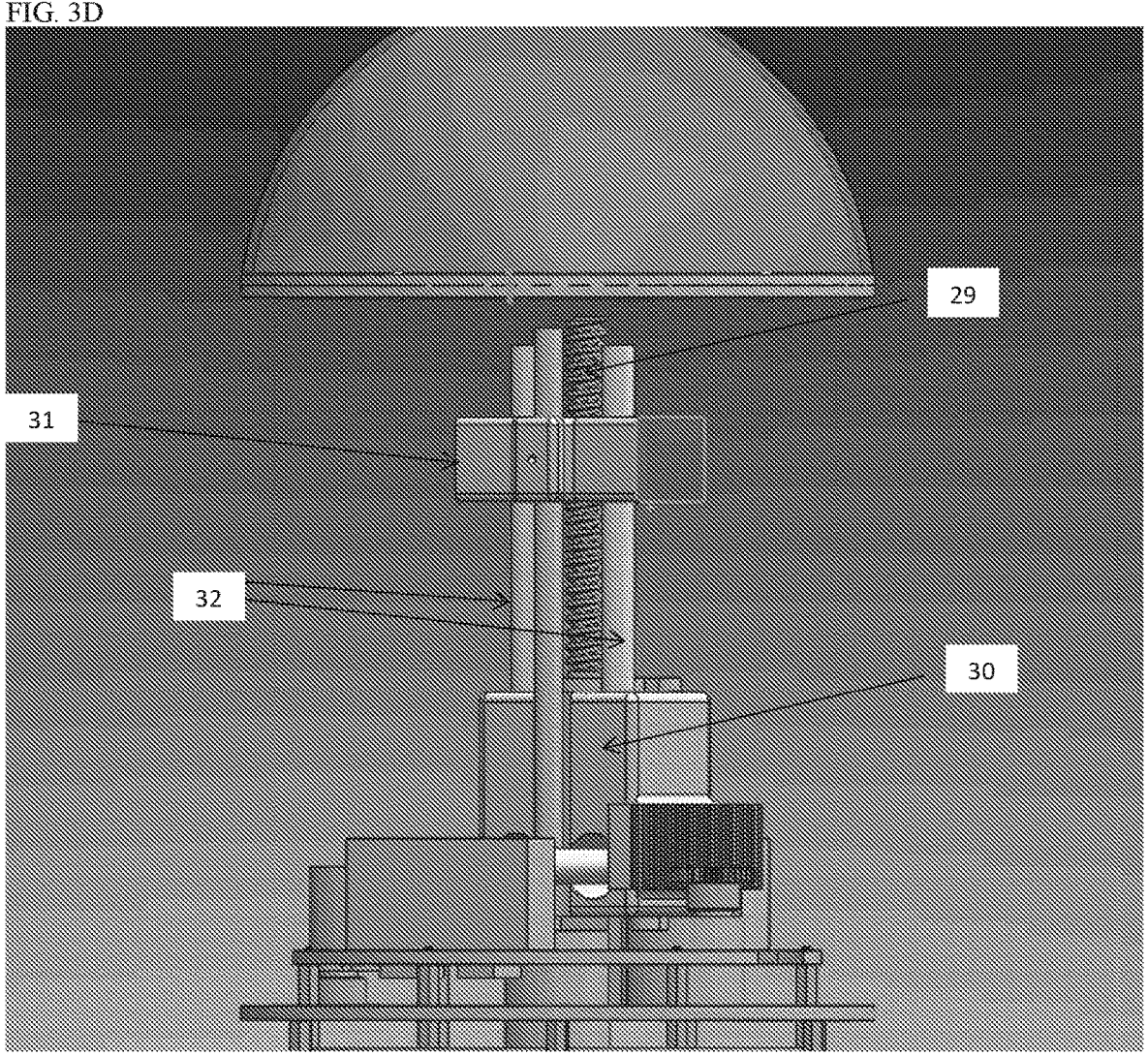

Z motion is shown in FIG. 3D. An ACME screw 29 is attached to a third stepper motor 30. As the motor turns the screw, the carriage 31 movies positively or negatively along the Z-axis. The Z carriage rides on two rails 32, thus maintaining microscope position.

The present disclosure is not limited to particular sample containers. In some embodiments, the sample container is a dish (e.g., petri dish, square dish), plate (e.g., 6 well, 12 well, 24 well, 48 well, 96 well, 348 well, 1536 well, etc.), bottle, roller bottle, container, flask (e.g., triangular, rectangular, modified triangular, or U-shape flask), multi-layer flask, spinner flask, bioreactor, or other solid support or liquid culture container.

Figure 4A:
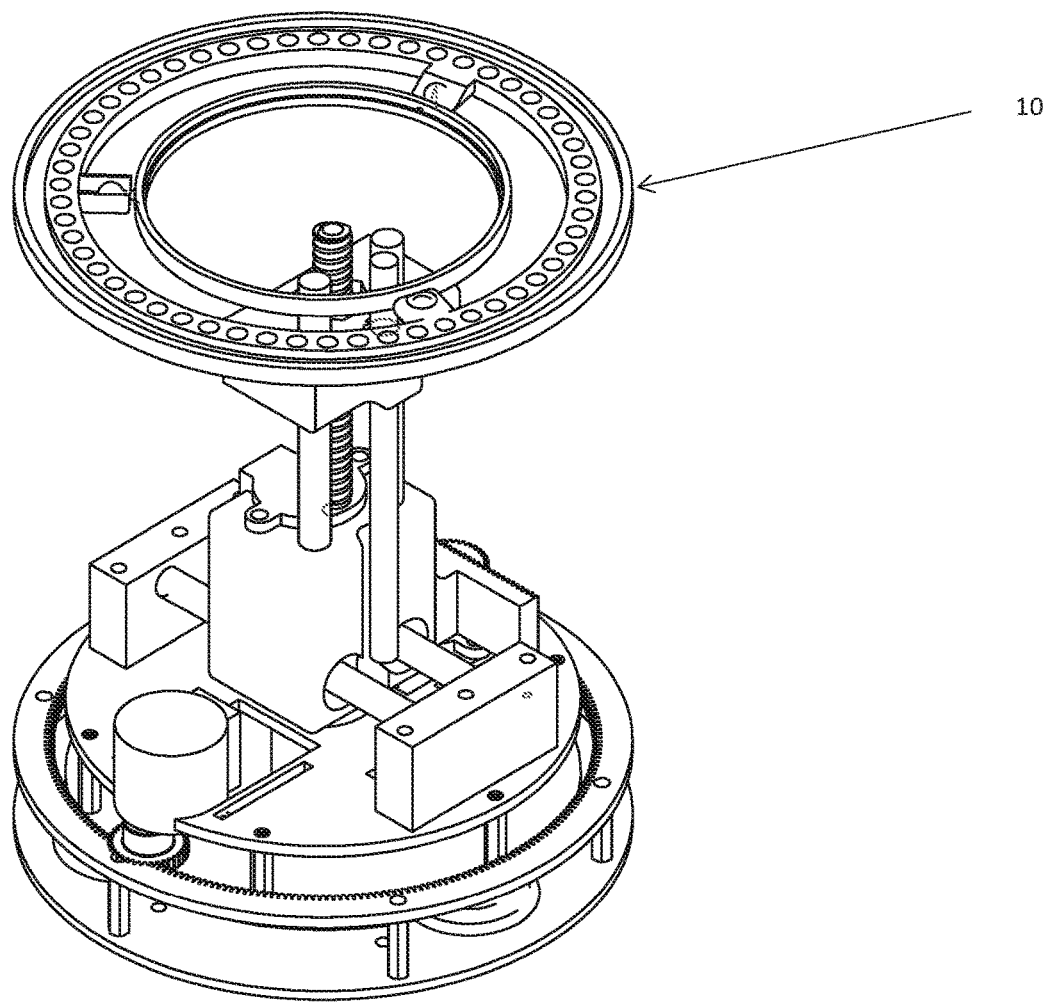
FIG. 4A-FIG. 4B shows exemplary sample holder alignment components of embodiments of the present disclosure.
Figure 4B:
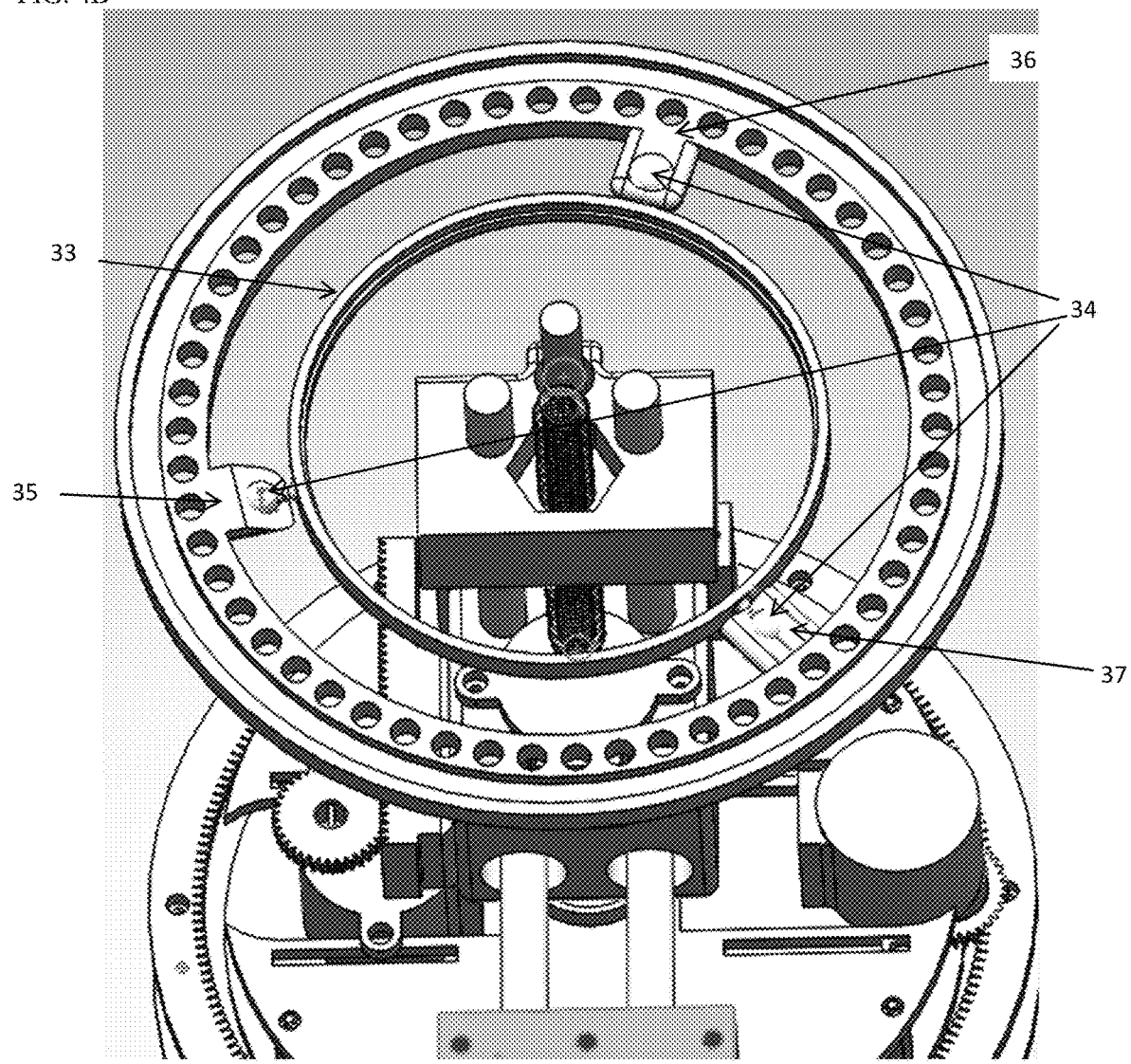

In some embodiments, modules comprise a cell culture sample alignment component 10 as shown in FIG. 4. FIG. 4A shows an overview of sample alignment component 10 integrated into a module. FIG. 4B shows details of the cell culture sample alignment component 10. Users often remove the sample container from the MVS module in order to add food (e.g., fresh media), administer drugs, etc. It is important that the user be able to replace the petri dish in precisely the same position so that measurements of target sites can continue. The component is illustrated with a petri dish as a sample container. However, the system can be modified for use with other sample containers and is not limited to use with a petri dish. In some embodiments, as shown in FIG. 4, the sample container alignment component utilizes a mounting ring 33 that can be snapped to a standard sample container (e.g., petri dish, not shown in FIG. 4B) that allows the dish to be precisely re-centered with minimal effort. Attached to the ring are three mounting "balls" 34: Ball one rests on a sloped plane 35; ball two rests in cone 36; ball three rests on a wedge 37. Unless all three locking mechanisms are engaged, the sample container will not rest properly. When properly aligned, the sample container drops into a stable configuration.

In some embodiments, specialized culture containers are employed comprising fiducials that align to or connect to corresponding structures on the alignment component 10 so as to ensure precise, reproducible fitting and alignment of a cell culture container to the imaging system.

Figure 5A:
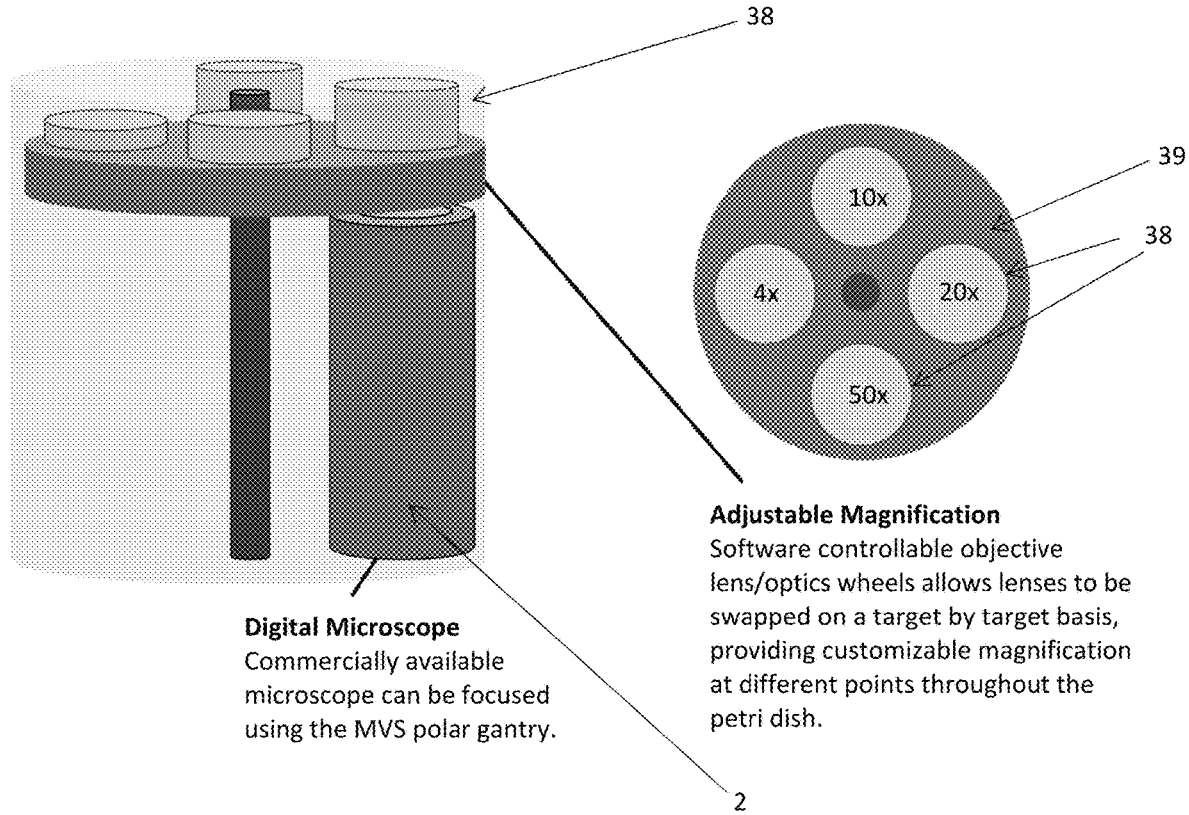
FIG. 5A-FIG. 5B shows exemplary configurable optical chain components of embodiments of the present disclosure.
Figure 5B:
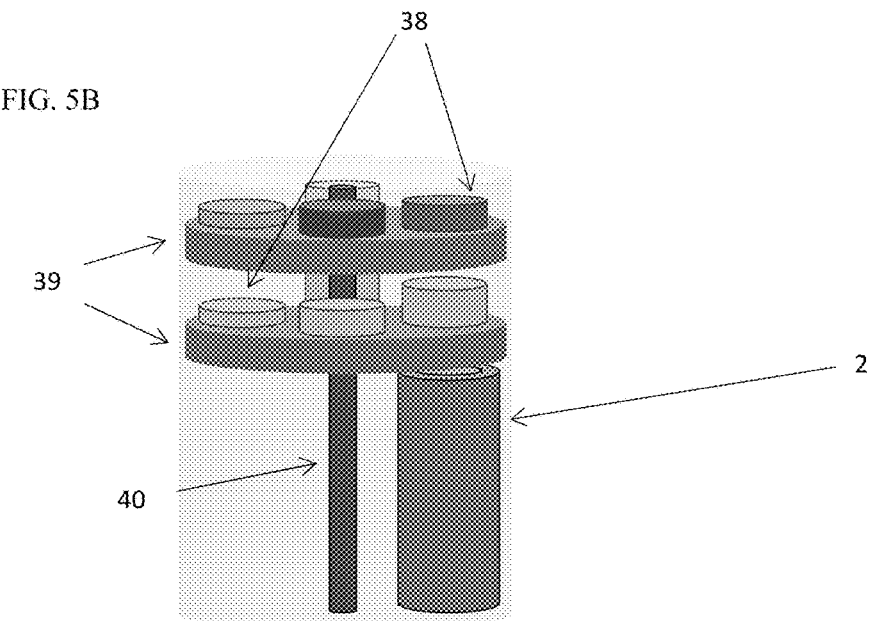

In some embodiments, modules comprise one or more optional optical elements as shown in FIG. 5. As shown in FIG. 5A, in some embodiments, the optical element comprises a plurality of different configurable optical elements (e.g., magnification (lenses), filters, half-wave plates, or other optical elements) 38. In some embodiments, the optical elements are provided in one or more wheels 39 in-line with the camera 2 on support 40. FIG. 5B shows an embodiment where a module comprises multiple wheels 39 containing optical elements 38 (e.g., one wheel comprises optical lenses for magnification and the second wheel comprises filters, although other configurations are specifically contemplated).

In some embodiments, the optical elements are configurable (e.g., via the user interface) to allow for different magnification, wavelength sensitivity, filters (e.g., for fluorescence microscopy), phase contrast, etc. in a single experiment. The optical properties of the microscope can be adjusted at any time during the experiment. This allows the user to effectively use multiple levels of magnification, optical, infrared, or UV wavelengths, and different microscopy modes on different targets in the same petri dish, without manual intervention.

In some embodiments, imaging components have distinct features relative to other imaging components, such as distinct camera types, magnification capabilities, light sources (e.g., fluorescence), filters, phase contrasts, etc. As such an individual imaging component may be optimal for certain uses while other imaging components having different features are optimal for other uses. The system allows mixing-and-matching of different imaging components. This provides users with tremendous flexibility in imaging capabilities. For example, two or more different imaging components may be employed in an incubator to provide two or more different measures of a sample. Additionally, two or more different imaging components may be employed in an incubator to separately analyze different samples, each needing a unique type of analysis. For example, six different imaging components may be used to run six different experiments simultaneously in the same incubator.

In some embodiments, modules comprise climate control components (e.g., waterproofing) to allow for use inside an incubator. The present disclosure is not limited to particular waterproofing components. In some embodiments, individual components are commercially obtained (e.g., cameras) that have been manufactured to be waterproof or water resistant. In other embodiments, the module and platform components comprise additional waterproofing components (e.g., waterproof covers or casing). Examples of waterproofing methods include, but are not limited to, seals, gaskets, fused joints, and the use of hydrophobic coatings.

In some embodiments, the modules in a system are the same or different. For example, in some embodiments, a system comprises a plurality of modules, wherein each of the modules is the same. In some embodiments, a system comprises different modules (e.g., one or more of each type of module).

In some embodiments, modules comprise all components needed to function fully (e.g., independent of a module holder) such as, for example, power and communication components, along with additional components described herein.

B. Module Holder

In some embodiments, the systems of the present disclosure utilize a module holder (e.g., universal platform) comprising a plurality of modules (e.g., a variety of the same or different modules) In some embodiments, each system comprises at least 2 (e.g., 3, 4, 5, 6, 7, 8, 9, 10 or more) modules. In some embodiments, the modules are arranged in an array on a universal platform, where the platform provides an interface with the modules that allows for the individual controlling of the zoom, movement, and light source of each camera. Each module within the holder is independently controlled, allowing for multiplexing of a variety of different experiments within a single system.

Figure 6A:
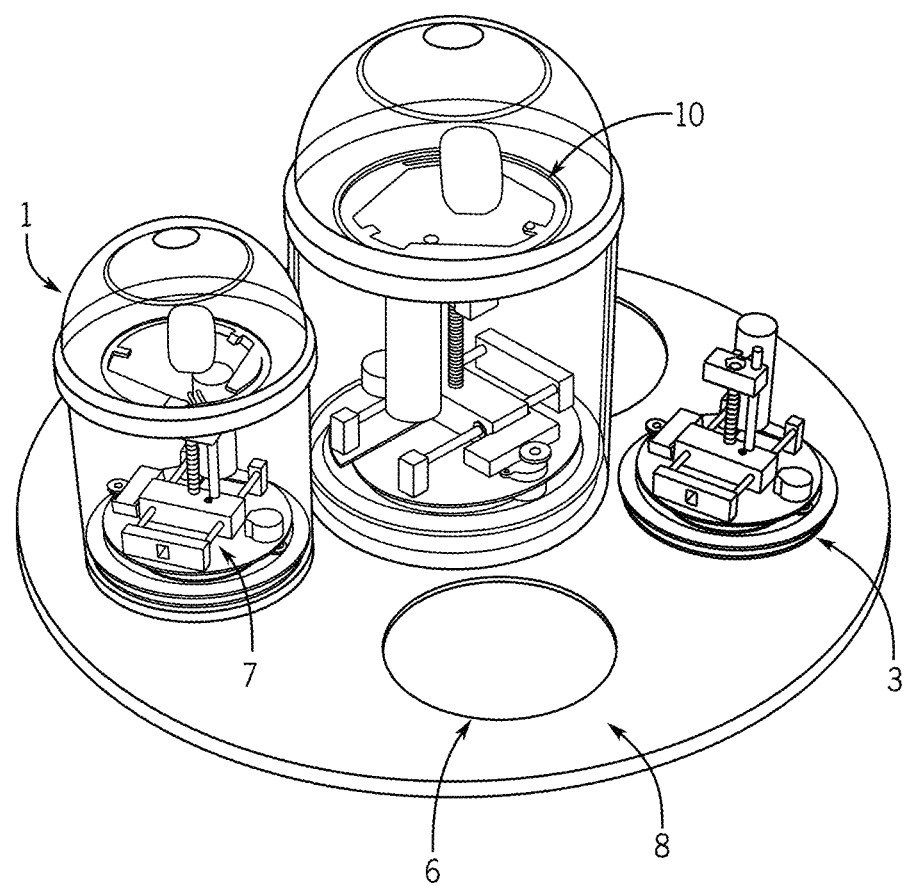
FIG. 6A-FIG. 6B shows exemplary module holder components of embodiments of the present disclosure.
Figure 6B:
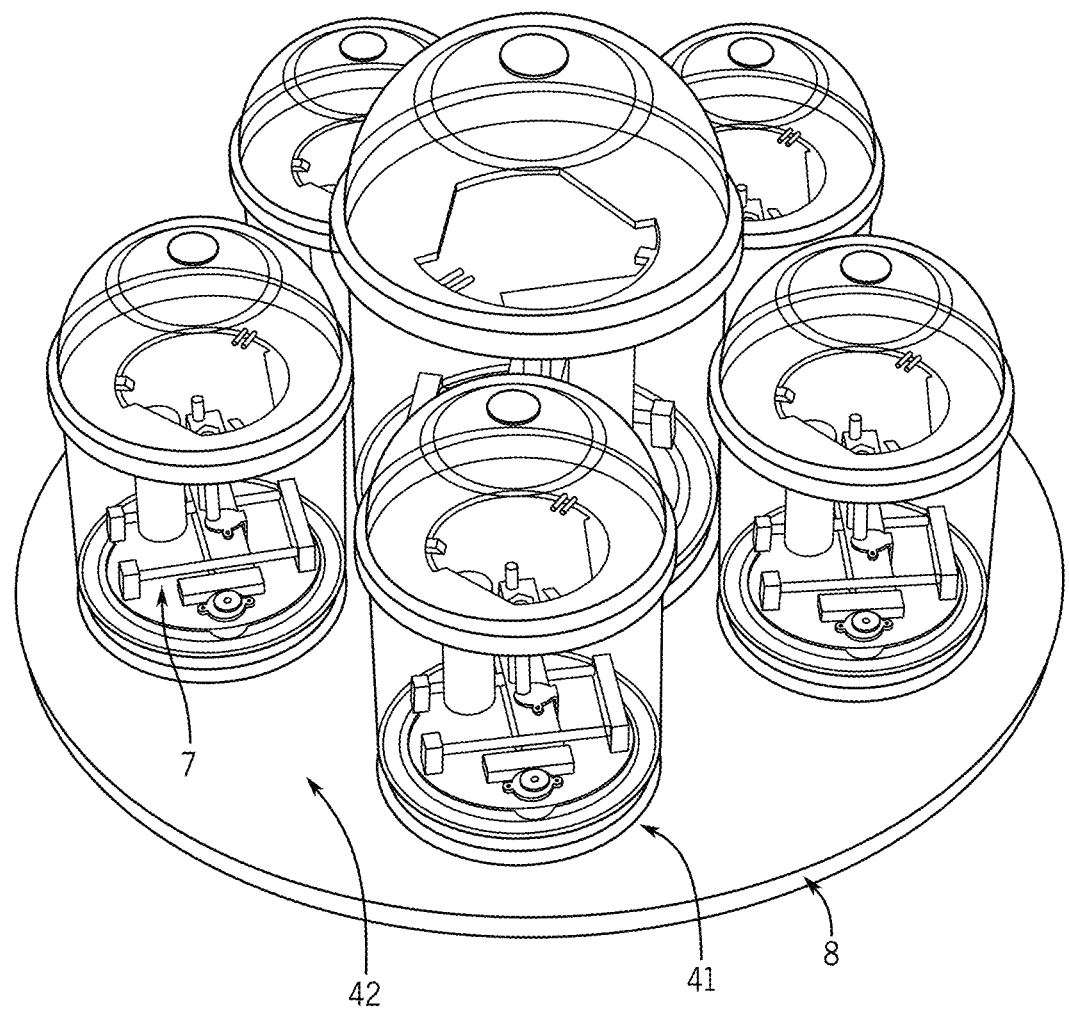

An exemplary module holder 8 is shown in FIG. 6. FIGS. 6A and B show a module holder 8 comprising modules 1 with waterproof cover or casing 7, gantry 3, sample holder alignment component 10, and waterproof attachment 6. Also shown is rotating component 42 and module connection 41.

In some embodiments, the module holder rotates via rotating component 42. In some embodiments, the module holder is waterproof (e.g., using components described above).

In some embodiments, the module holder (e.g., platform) serves as a power supply/recharge station for each module, as well as a data relay station that communicates with an external user interface. In some embodiments, the connection between the module and the platform is protected (e.g., waterproof). In some embodiments, the module holder and/or modules comprises a signal amplification/satellite antennae system to extract the signal from the system. In some embodiments, each module is physically connected to the platform. In some embodiments, the modules and/or module holder are hard wired (e.g., platform to computer). In some embodiments, the platform serves as a hard-drive for data storage, allowing for the system to be utilized in an extreme condition such as underwater, to gather data, and the data is transferred to the computer via hard-wire or wirelessly when appropriate at a later time.

C. User Interface

There are unique challenges inherent in controlling multiple digital microscope cameras such as the number of cords exiting the system, supplying power to each module, lighting, memory, data triaging, data transfer rates, etc. The universal platform of embodiments of the present disclosure facilitates these functions. In some embodiments, the system utilizes just one cord/or no cords (e.g., wireless communication such as Bluetooth or Wi-Fi) exiting the system that can connect directly to a laptop or other computing system. In some embodiments, each module comprises a miniature computer (micro-controller e.g. raspberry pi, arduino, etc.), and interfaces with the platform. The platform, in turn, then amalgamates the signals from each module and interfaces with the computer via an Ethernet port or via Wi-Fi.

The present disclosure is not limited to particular user interfaces. In some embodiments, the user interface is a laptop computer, a desktop computer, a tablet, a smart watch, or a smart phone.

In some embodiments, the user interface comprises software configured to control operation of the modules, incubation components, and module holder. In some embodiments, the software is configured to obtain images or video of samples at a predetermined time interval or intervals. In some embodiments, a portion of or the entire sample is imaged. In some embodiments, one or more of the modules is independently activated. In some embodiments, the software is configured to control the frequency and location of images of the cell culture, analyze image data, analyze expression of markers or genes of interest, and/or control the operation of the modules, incubation components, and the module holder. In some embodiments, the software allows users to create videos, replay videos at different speeds, annotate these videos, improve image quality, and make quantitative and qualitative measurements of the cell culture development.

In some embodiments, the system provides user interface software that allows a user to design or select system parameters needed or useful to run one or more experiments. For example, in one embodiment, a user turns on a computing device that provides a user interface. The user interface provides a menu of options. In some embodiments, the user selects settings that identify the number of and/or nature of the imaging modules that are to be used in an experiment. In some embodiments, no such entry is required, but rather placement of imaging modules into the system provides auto-recognition of the number and type of imaging modules. This may be accomplished by bar codes, chips, or other features on the imaging modules that identify the nature of the module. The module holder may include sensors that identify whether a module has been placed in any one of a plurality of locations on the module holder. In some embodiments, the user interface provides a menu of control options for the module identified, allowing the user to select particular parameters of the hardware (e.g., filters, camera locations, etc.) and the experiment to be conducted (e.g., timing of image or video capture). In some embodiments, the user interface accesses a database of pre-established experimental protocols and allows the user to select from a menu of such options. In some embodiments, the user interface permits the user to design and save new protocols.

D. Incubation

The microscope surveillance system described herein is a modular, multi-functional microscopy system suitable for use in incubators and other environments. In some embodiments, as described above, modules and modules holders are placed in an incubator. In other embodiments, individual modules or module holders comprise incubation systems. For example, in some embodiments, systems comprise multiple (2-10+) modules, where each module is equipped with an incubation system. This facilitates removal of the module from a standard incubator for personalized experimentation from any location. Incubating multiple modules has several advantages over in-incubator only systems. Current in-incubator-only live cell imaging systems require multiple users to use one incubator, increasing the likelihood of culture contamination and experimental interference. Additionally, with in-incubator-only live cell imaging systems, multiple users are expected to align experimental schedules over prolonged time periods, so that the imaging can proceed without interruption longitudinally. Incubating individual modules also facilitates portability, which broadens the scope of applicability of the microscope surveillance system. For example, the unit can be utilized as a point of care imaging instrument for the collection of bodily fluids (saliva, blood, urine, etc.) from clinical patients, with the advantage of immediately monitoring cell behavior for diagnostic or treatment purposes.

A standard laboratory cell culture incubator provides $CO_2$, heat, and humidity at regulated levels for optimal cell growth. The standard levels of $CO_2$, heat, and humidity within incubated settings are: 5% $CO_2$, 37° C., and 95% humidity. These levels are typically maintained by providing a replenishable reservoir of $CO_2$ and water, and by providing a continuous heating source. The levels are then regulated by sensors within the incubator. $CO_2$ is commonly delivered via a direct supply line connected to a commercially available tank system. In some cases, research buildings are equipped with internal $CO_2$ generators and plumbing, which provide a direct source of $CO_2$ for multiple incubators.

$CO_2$ generation for biomedical research is a formidable industry which imparts many costly negative global environmental consequences and inconveniences. The production of $CO_2$ is an energy consuming process, and the subsequent bottling and distribution of $CO_2$ tanks increases the carbon footprint even further. While cells in incubators utilize $CO_2$ for survival, not all of the delivered $CO_2$ is used by the cells. Every time an incubator door is opened, $CO_2$ escapes into the surrounding atmosphere. This amount of $CO_2$ loss is not trivial when considering how many times in a day this occurs, and how many incubators exist. Taken together, the production, delivery, and inefficient use of $CO_2$ in research laboratories produces a significant amount of $CO_2$ that is lost to the environment.

During the development of modules comprising incubation systems described herein, obstacles related to various aspects of the incubation modules were overcome. For example, the volume of incubation within a module is orders of magnitude smaller than the volume of a standard incubator or microscope stage incubation system. This provides a need and an opportunity for efficiency, since only a small volume of $CO_2$, water, and heat are needed to maintain optimal incubation settings. Size also presents an obstacle as most of the module housing is occupied by the gantry system. The systems described herein address these obstacles by incorporating functional reservoirs, microsensors, and delivery channels for $CO_2$ and water. The systems utilize either external supply lines, avoid excessive manual input from the user to replenish reservoirs, and/or incorporate self-renewing technologies for water and $CO_2$ removal from ambient air. Described herein are exemplary, non-limiting methods for the incorporation of incubation within the microscope surveillance system.

In some embodiments, an incubation environment is provided by external gas and water connections to the module holder. In some embodiments, module holder systems comprise self-renewing $CO_2$ and $H_2O$ systems or external reservoirs.

Figure 7:
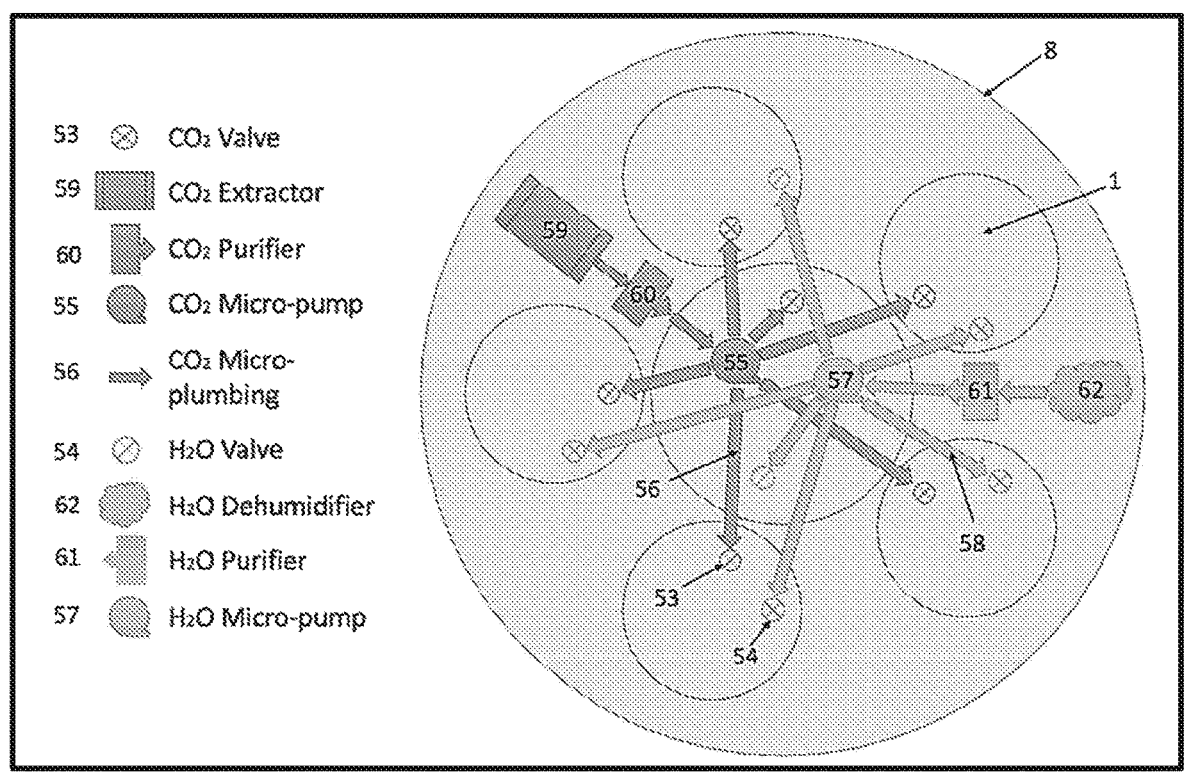
FIG. 7 shows an exemplary incubation system within a universal stage with incorporated embodiments of the present disclosure.

Now referring to FIG. 7, shown is module holder 8 and a plurality of modules 1. In some embodiments, the module holder is connected to an external gas and water source (not shown in FIG. 7), and the elements are then pumped into the module upon connection to the stage via one-way valve systems. In FIG. 7, shown are $CO_2$ valves 53 and $H_2O$ valves 54. Still referring to FIG. 7, in some embodiments, the $CO_2$ valves 53 and $H_2O$ valves 54 are in operable communication with $CO_2$ micro-pumps 55 and $CO_2$ micro-plumbing 56 and $H_2O$ micro-pumps 57 and $H_2O$ micro-plumbing 58. In some embodiments, the micro-pumps 55 and 57 and micro-plumbing 56 and 58 are operably linked to one or more of $CO_2$ extractor 59, $CO_2$ purifier 60, $H_2O$ purifier 61 and $H_2O$ dehumidifier 62.

Figure 8:
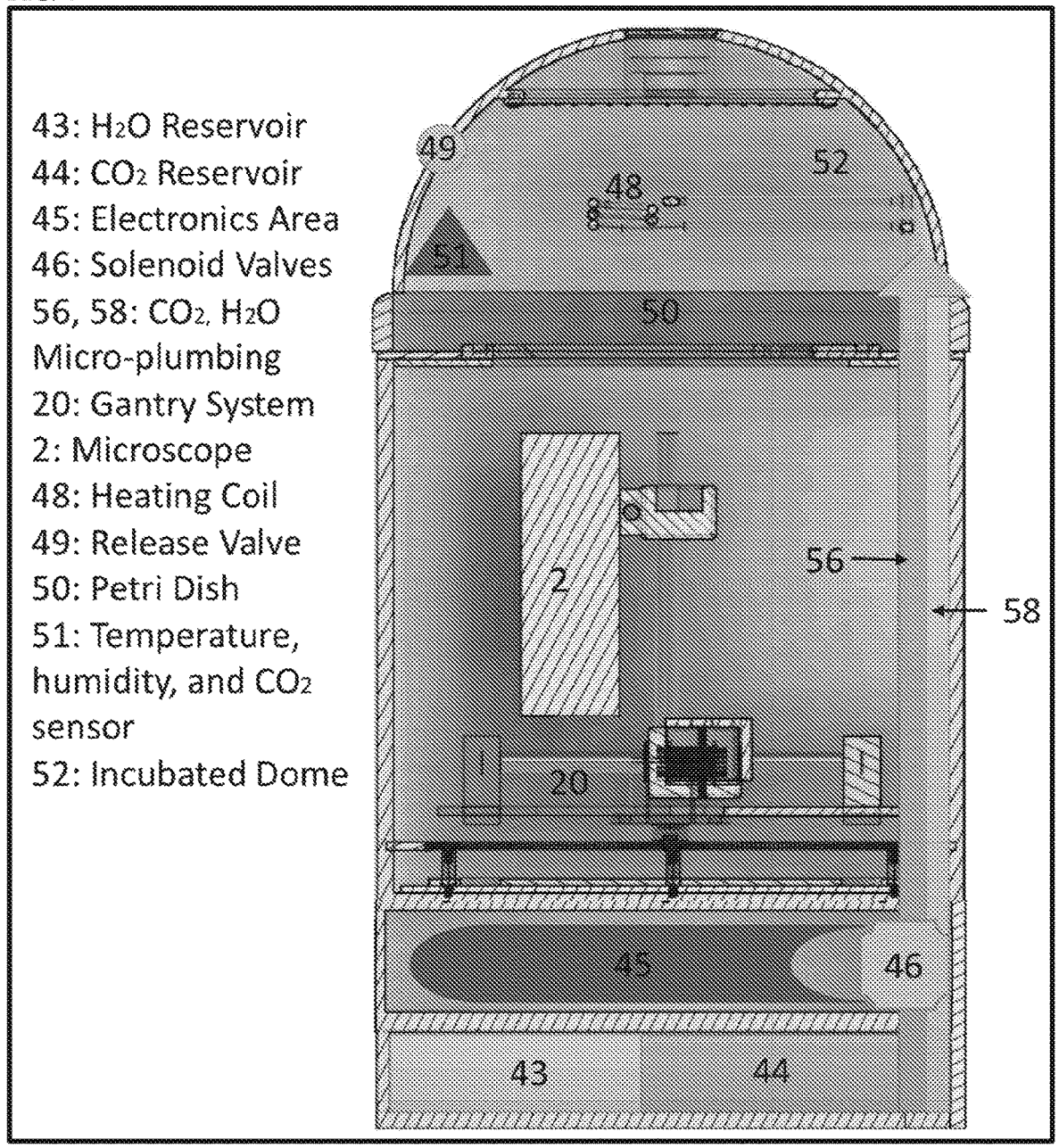
FIG. 8 shows a schematic of an exemplary incubated module of embodiments of the present disclosure.

Alternatively, individual modules contain miniature reservoirs in operable communication with micro-pumps 55 and 57 and micro-plumbing 56 and 58, which are filled, enabling removal from the stage for module portability. FIG. 8 shows an exemplary module 1 comprising internal $H_2O$ reservoir 43, internal $CO_2$ reservoir 44 in operable communication with solenoid valve 46 and micro-plumbing 56 and 58. The solenoid valve 46 pumps $H_2O$ and $CO_2$ from reservoirs 43 and 44 through micro-plumbing 56 and 58 into the incubated dome 52. The delivery of $CO_2$ and $H_2O$, along with maintenance of other components of the incubation system is controlled by electronics 45. In some embodiments, each module contains a dedicated heat source 48, sensors 51, and microcontrollers (e.g., electronics 45) for monitoring and controlling temperature, humidity and $CO_2$ levels. FIG. 8 also show gantry system 20, release valve 49, and petri dish 50.

In some embodiments, an individual module(s) contains connection sites for external gas and water sources. Micro-pumps and microvalves (e.g., as shown in FIG. 7) then pump the elements into the incubation chamber according to the settings requested. As with normal incubators, the length of the recording is limited only to the size of the external reservoir; which requires less repetitive oversight from the user.

In some embodiments, an incubation environment is provided by external self-sustaining gas and water supplies. For example, in some embodiments, water is extracted from the ambient air via an external de-humidifier and stored in the module reservoir. When needed, a humidifier supplies the module with the required humidity level. Similarly, in some embodiments, direct $CO_2$ capture is accomplished through the miniaturization of chemical techniques (See e.g., Keith et al., 2006 Climatic Change, 74(1-3), pp. 17-45; Keith et al., 2018. Joule, 2(8), pp. 1573-1594; Keith et al., 2015. U.S. Pat. No. 9,095,813; and David Keith: Carbon Engineering—Industrial-scale capture of $CO_2$ from ambient air www.youtube.com/watch?v=GkEAA7VnyhE; each of which is herein incorporated by reference in its entirety) using potassium hydroxide desiccants. In this method, ambient air contacts a potassium hydroxide solution to form potassium carbonate. Heated potassium carbonate releases both water and pure $CO_2$, both of which are required for adequate incubation. Potassium oxide remnants are then mixed in water to re-form potassium hydroxide. The entire process only requires 0.163 kWhr per pound (454 g) of $CO_2$ produced, and costs 4.7-11.6 cents per pound to produce. The incubation chamber within the dome of the microscope surveillance module is approximately 450 cc. Therefore, at NTP, the module only requires 25 ml of $CO_2$ to fill the module at 5%, In comparison, conventional laboratory incubators have incubation chambers ranging from 50,000-300,000 cc. Filling these chambers requires between 2,500-15,000 ml of $CO_2$. The general chemistry is outlined as follows:

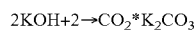
$$2KOH + 2 \rightarrow CO_2 * K_2CO_3$$

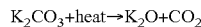
$$K_2CO_3 + heat \rightarrow K_2O + CO_2$$

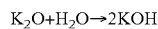
$$K_2O + H_2O \rightarrow 2KOH$$

*Boric Acid is used as an expediting reagent (Smith et al., 2012 International Journal of Greenhouse Gas Control, 10, pp. 64-73 and Ghosh et al., 2009. Energy Procedia, 1(1), pp. 1075-1081; each of which is herein incorporated by reference in its entirety).

Although this is an efficient and inexpensive form of $CO_2$ capture the reactants are corrosive, and heat is required to expel $CO_2$ gas from carbonate. These factors necessitate an external chamber for $CO_2$ production.

In some embodiments, an incubation environment is provided by internal self-sustaining gas and water supplies. In this embodiment, the water capture method is as described above, however the $CO_2$ capture is accomplished through the use of ion exchange resins (IER) (See e.g., Lackner and Wright: www.youtube.com/watch?v=JUSSTYJsIXQ and Armstrong et al., 2019 AIChE Journal, 65(1), pp. 214-220; each of which is herein incorporated by reference in its entirety). In some embodiments, the IERs is a strong base (e.g., functionalized with trimethylamnionium groups, e.g. polyAPTAC) that absorbs $CO_2$ when dry and emits $CO_2$ when wet. To increase the surface area for gas exchange, the polymer is coated onto a polypropylene sponge. The module dome is equipped with a water reservoir and slow rotation device to move the resin-coated polypropylene sponge from the water reservoir to the dry area and back again. Drying of the sponge is accomplished both mechanically, with squeezing rollers, and with an internal heating coil and fan. During rotation in the dry phase, the sponge also comes into contact with the ambient air outside of the dome through a movable filter that opens when in contact with the sponge. This facilitates acquisition of more $CO_2$. This mechanism is self-sustaining, in that as long as there is a constant water and drying mechanism in place, the resin does not need to be replaced. In addition, this mechanism does not require substantial heat, therefore the entire mechanism exists within the module dome, without need for external chambers. Approximately 25-50 cc of the resin-coated polypropylene sponge is required to supply 5% $CO_2$ at a constant rate with this method, depending on the rate of revolution around the module. Exposure of 50cc of the dry resin-coated polypropylene sponge to ambient air for approximately 150 seconds accumulates 25 cc of $CO_2$, which is enough to fill the volume of the dome with 5% $CO_2$. Lastly, Purolite is commonly used in water purification systems, and as such, it is readily available and inexpensive (Approximately \$300-\$500 for 45 lbs.).

Figure 9A:
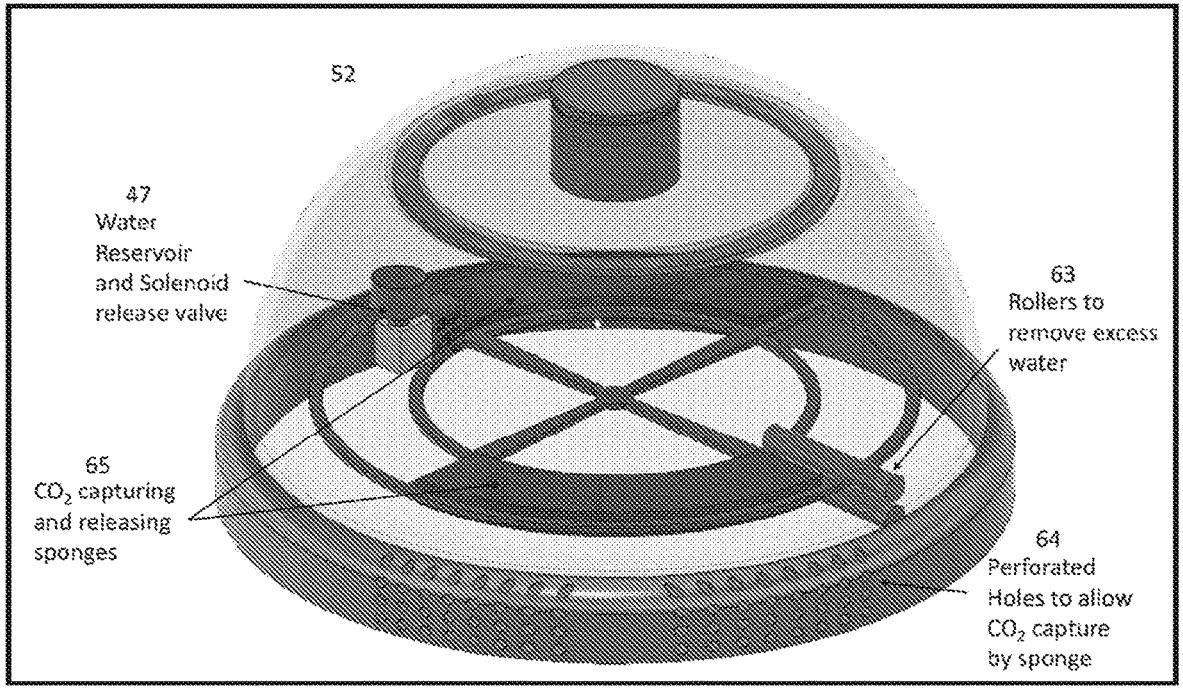
FIG. 9A shows a profile view of an incubated dome with embodiments of a self-sustaining $CO_2$ capture device and FIG. 9B a worms-eye view of the system with embodiments of a self-sustaining $CO_2$ capture device.
Figure 9B:
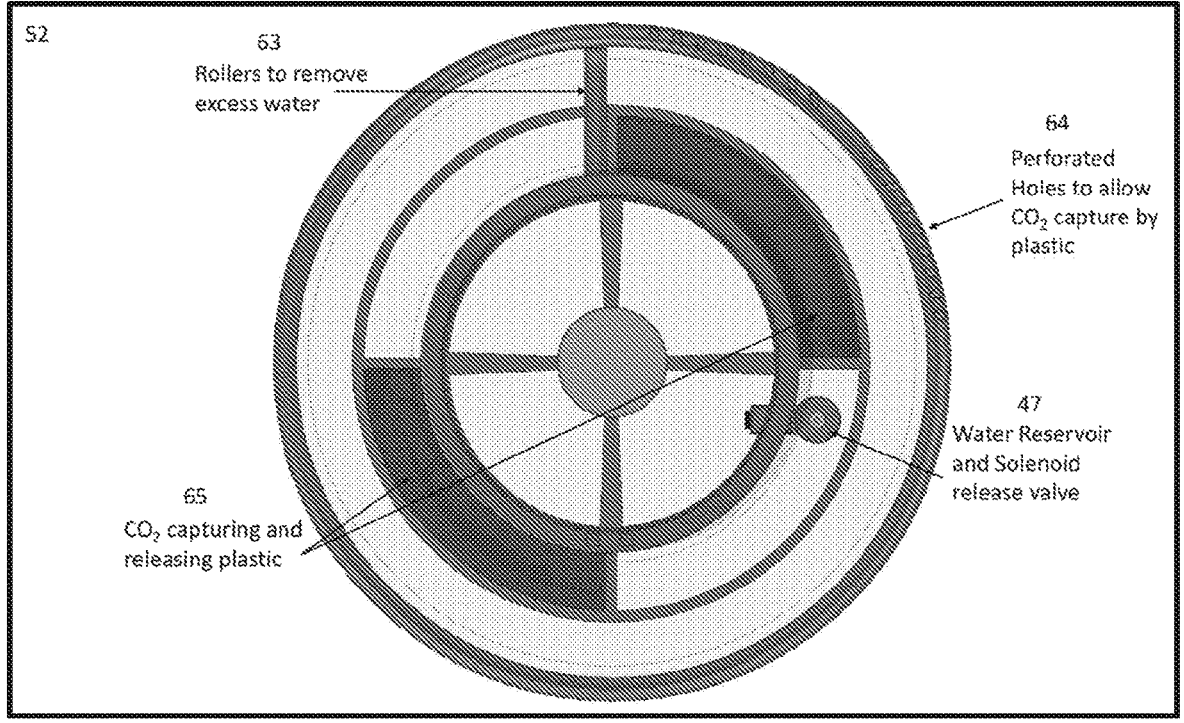

FIGS. 9A-B show an exemplary incubation dome with internal self-sustaining gas and water supplies. Referring to FIG. 9A, shown is a side view of incubated dome 52. Shown is water reservoir and solenoid release valve 47. Still referring to FIG. 9A, shown is $CO_2$ capturing and releasing sponges 65 comprising IER, rotation component and drying rollers 63, and perforated holes 64.

Now referring to FIG. 9B, shown is a bottom view of incubated dome 52. Shown is water reservoir and solenoid release valve 47. Still referring to FIG. 9B, shown is $CO_2$ capturing and releasing sponges 65 comprising IER, rotation component and drying rollers 63, and perforated holes 64.

As described above and illustrated in FIGS. 9A-B, the water reservoir 47 and slow rotation component move the resin-coated polypropylene sponge 65 from the water reservoir 47 to the dry area and back again. Drying of the sponge is accomplished both mechanically, with squeezing rollers 63, and with an internal heating coil and fan (not shown).

II. Uses

The systems of the present disclosure find use in a variety of applications (e.g., diagnostic, screening, and research applications). In some embodiments, the systems are used to monitor the growth of cells (e.g., eukaryotic cells (e.g., single celled organisms, immortalized cell lines, primary cell lines, stem cells, and the like), tissues, or prokaryotic (e.g., bacterial) cells) in culture.

In some embodiments, the systems find use in analyzing cells in culture. For example, in some embodiments, assays are performed on cells in the system to determine the presence of an analyte in a sample (e.g., biological sample), expression of a marker or gene of interest, response to a drug or other intervention or treatment, etc.

All publications and patents mentioned in the above specification are herein incorporated by reference in their entirety. Various modifications and variations of the described devices, methods and/or systems will be apparent to those skilled in the art without departing from the scope and spirit of the disclosure. Although the disclosures have been described in connection with specific preferred embodiments, it should be understood that the disclosures as claimed should not be unduly limited to such specific embodiments. Indeed, various modifications of the described modes for carrying out the disclosures which are obvious to those skilled in the relevant fields are intended to be within the scope of the following claims.

We claim:

1. An imaging system comprising: a) at least 3 distinct imaging modules each comprising i) an imaging component, ii) a sample container; and iii) a waterproof casing and configured for image or video capture of a cell culture sample placed in a said sample container; b) a user interface, external to said modules, configured to receive image or video data from each of said plurality of different imaging modules; c) a module holder configured to individually position each of imaging modules; d) an incubation component.

2. The system of claim 1, wherein said imaging modules comprise one or more components selected from the group consisting of a digital microscope camera in operable communication with a camera motion control component, a cell culture sample alignment component, a configurable optical element component, a computer processor, a power source, a communication component, and a light source.

3. The system of claim 2, wherein said camera motion control component comprises a robotic element that is configured to move said camera in X, Y, and Z dimensions.

4. The system of claim 3, wherein said robotic element comprises a cylindrical gantry.

5. The system of claim 2, wherein said cell culture sample alignment component comprises a sample container mounting ring configured to attach to said sample container and a mounting component configured to align and attach to said sample container mounting ring.

6. The system of claim 5, wherein said mounting component comprises a plurality of mounting balls.

7. The system of claim 2, wherein said configurable optical element component comprises a software configurable optical element wheel in optical communication with said digital microscope camera.

8. The system of claim 7, wherein said configurable optical element comprises a plurality of different objective lenses, filters, or half wheel plates.

9. The system of claim 1, wherein said sample container is a petri dish.

10. The system of claim 9, wherein the alignment of said configurable optical element is configured for operation remotely.

11. The system of claim 9, wherein said system comprises a plurality of different configurable optical elements.

12. The system of claim 1, wherein said modules are independently configured to perform one or more of visible light microscopy and fluorescence microscopy.

13. The system of claim 1, wherein said modules are independently configured to collect qualitative or quantitative data and transmit said data to said user interface.

14. The system of claim 1, wherein said system is configured to obtain images or video of said sample at a predetermined interval.

15. A method of imaging a cell culture sample, comprising:
a) contacting said sample with the system of claim 1, and
b) collecting imaging data related to said sample using said system.

16. The system of claim 1, wherein said incubation component is an incubator configured to house said imaging modules and said module holder.

17. The system of claim 1, wherein said incubation component comprises external sources of $CO_2$ and $H_2O$ in operable communication with said module holder or one or more of said modules.

18. The system of claim 1, wherein said incubation component comprises sources of $CO_2$ and $H_2O$ located inside one or more of said modules.

19. The system of claim 18, wherein said incubation component further comprises a $CO_2$ capture component comprising a chemical $CO_2$ generation component and/or a ion exchange resin component.

* * * * *

UNITED STATES PATENT AND TRADEMARK OFFICE
CERTIFICATE OF CORRECTION

PATENT NO. : 11,762,184 B2
APPLICATION NO. : 17/259073
DATED : September 19, 2023
INVENTOR(S) : Alexis Donneys, Alexis Baker and Steven R. Buchman It is certified that error appears in the above-identified patent and that said Letters Patent is hereby corrected as shown below:

In the Claims

Claim 1, Column 15, Line 29 reads:
"sample placed in a said sample container; b) a user interface,"

Whereas it should read:
"sample placed in said sample container; b) a user interface,"

Signed and Sealed this
Twenty-sixth Day of March, 2024

Katherine Kelly Vidal
*Director of the United States Patent and Trademark Office*